(12) United States Patent
Dussarrat et al.

(10) Patent No.: US 7,807,223 B2
(45) Date of Patent: Oct. 5, 2010

(54) PRECURSORS HAVING OPEN LIGANDS FOR RUTHENIUM CONTAINING FILMS DEPOSITION

(75) Inventors: Christian Dussarrat, Wilmington, DE (US); Julien Gatineau, Tsukuba (JP)

(73) Assignee: L'Air Liquide Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 408 days.

(21) Appl. No.: 11/835,968

(22) Filed: Aug. 8, 2007

(65) Prior Publication Data

US 2008/0107812 A1    May 8, 2008

(30) Foreign Application Priority Data

Aug. 8, 2006   (EP)   .................................... 6300864

(51) Int. Cl.
*C23C 16/18*   (2006.01)
*C23C 16/40*   (2006.01)

(52) U.S. Cl. .................................. 427/250; 427/255.31

(58) Field of Classification Search .................. 427/250, 427/255.31
See application file for complete search history.

(56) References Cited

U.S. PATENT DOCUMENTS 6,605,735 B2   8/2003   Kawano et al.
6,818,783 B2 *  11/2004  Norman et al. ............. 556/112
2004/0166671 A1   8/2004  Lee et al.
2004/0241321 A1 * 12/2004  Ganguli et al. ......... 427/255.28
2005/0033075 A1 *  2/2005  Chi et al. .................... 556/117
2008/0237861 A1 * 10/2008  Dominguez et al. ......... 257/751
2009/0022958 A1 *  1/2009  Plombon et al. ............ 428/164

FOREIGN PATENT DOCUMENTS

| EP | 1 293 509 |  | 3/2003 |
| EP | 1293509 A2 | * | 3/2003 |
| WO | WO 2005 020317 |  | 3/2005 |
| WO | WO 2008/088563 A2 | * | 7/2008 |

OTHER PUBLICATIONS

Li Huazhi, et al., "Vapor Deposition of Ruthenium from an Amidinate Precursor". Journal of the Electrochemical Society, 154, (12) D642-D647 (2007).*
European Search Report for EP 06 30 0864.
Lee, John P. et al. *"Reactions of a Ru(II) phenyl complex with substrates that possess C-N or C-O multiple bonds: C-C bond formation, N-H bond cleavage, and decarbonylation reactions,"*Organometallics, Mar. 13, 2006, vol. 25, No. 6, pp. 1500-1510.

* cited by examiner

*Primary Examiner*—Bret Chen
(74) *Attorney, Agent, or Firm*—Patricia E. McQueeney

(57) ABSTRACT

Ruthenium containing precursors for ruthenium containing films deposition comprising a ruthenium precursor selected from the group essentially consisting of $Ru(XOp)(XCp)$, $Ru(XOp)_2$, $Ru(allyl)_3$, $RuX(allyl)_2$, $RuX_2(allyl)_2$, $Ru(CO)_x$(amidinate)$_y$, $Ru(diketonate)_2X_2Ru(diketonate)_2$(amidinate)$_2$, their derivatives, and any mixture thereof.

1 Claim, No Drawings

PRECURSORS HAVING OPEN LIGANDS FOR RUTHENIUM CONTAINING FILMS DEPOSITION

The invention relates to ruthenium precursors for ruthenium containing film deposition which are useful in semiconductor fabrication.

CROSS REFERENCE TO RELATED APPLICATIONS

This application claims the benefit of priority under 35 U.S.C. §119 (a) and (b) to European Application No. 06300864, filed Aug. 8, 2006, the entire contents of which are incorporated herein by reference.

BACKGROUND

Ruthenium is one of the most promising materials for capacitor electrodes for the next generation DRAM devices, as well as for barrier and/or seed layers between a copper layer and a Low-k dielectric layer. Now, high dielectric constant (high k) materials such as aluminum oxide ($Al_2O_3$) tantalum pentaoxide ($Ta_2O_5$) hafnium oxide and related materials, or Barium Strontium Titanate (BST) are used in capacitor cells and the process uses temperature up to 600° C. At such temperatures the oxidation of polysilicon, silicon, or aluminum occurs leading to capacitance loss. Ruthenium, as well as ruthenium oxide, have both high oxidation resistance and high electrical conductivity, and can be used as a capacitor electrode and an effective barrier against oxygen diffusion. Ruthenium is also used as a gate metal for lanthanide oxide. Besides, it is easily dry etched by ozone or by plasma techniques with oxygen, which is not the case of platinum and other noble metal compounds. Ruthenium may also be used as a barrier layer and a seed layer to separate a low-k material layer from an electrochemically deposited copper.

Many different precursors have been suggested to be used for ruthenium or ruthenium oxide layers deposition: Bis(ethylcyclopentadienyl)Ruthenium, [$Ru(EtCp)_2$], pure or dissolved in a solvent (e.g. tetrahydrofurane), is frequently used as a precursor: It is liquid at room temperature, with a vapor pressure of 0.1 Torr at 75° C. Ru or $RuO_2$ films are usually deposited using this precursor by CVD at temperatures between 300° C. to 400° C., and more recently by Atomic Layer Deposition (ALD), using oxygen as a reactant.

Ruthenocene ($RuCp_2$) which has a melting point around 200° C., is also one of the precursors frequently used to deposit Ru or $RuO_2$ in the same range of temperature as $Ru(EtCp)_2$, with the same reactant, by CVD or ALD.

Tris(2,4-octanedionato)ruthenium [$Ru(OD)_3$], which is liquid at room temperature and has a vapor pressure of 1 Torr at 200° C. is also used as a precursor by CVD deposition in a temperature range around 300° C.

US 2004/0241321 discloses "sandwiched" precursors, i.e., with the ruthenium atom centered around two of these Op ligands.

U.S. Pat. No. 6,605,735 discloses "half-sandwich" precursors with the ruthenium atom centered around one Op ligand and one cyclic-type (cyclopentadienyl for instance) ligand (The molecule, whatever the structure, has 18 electrons (8 from the Ru, 5×2 from the Op or Cp) and is thus stable.

There are several issues for the man skilled in the art when depositing a Ru or $RuO_2$ layer or film on a substrate:

(a) the poor adhesion of such layer/film to the substrate;

(b) the presence of impurities in the film deposits on that substrate: the presence of impurities such as carbon in the deposited layer increases the resistivity of the film. Other impurities such as oxygen, hydrogen, and/or fluorine are sometimes present in the deposited layer, depending on the precursor composition.

(c) the delivery of the Ru precursor product may not be easy, due to the low vapor pressure of these precursors, which are sometimes solid, also raise concerns.

(d) the incubation time of $Ru(EtCp)_2$. This incubation time may be reduced by using $Ru(dmpd)(EtCp)$. A sputtering deposition seed layer before Ru deposition is sometimes necessary to avoid this incubation time at the initial stage of the growth when using $Ru(EtCp)_2$ (e) some precursors have a very low volatility which decreases the deposition speed of the process.

Ruthenium films are often deposited on oxygen sensitive surfaces made of nitrides, or pure metal, such as Ta or TaN. The use of oxygen as a co-reactant is therefore undesired as it results in the partial oxidation of the underlying layer.

According to the invention, these (and other) issues are solved by the use of ruthenium precursors for ruthenium containing film deposition selected from the group comprising: $Ru(XOp)(XCp)$, $Ru(XOp)_2$, $Ru(allyl)_3$, $RuX(allyl)_2$, $RuX_2(allyl)_2$, $Ru(CO)_x(amidinate)_y$, $Ru(diketonate)_2X_2$, $Ru(diketonate)_2(amidinate)_2$ their derivatives and any mixture thereof.

The precursor used may be a mix of open and cyclic ligands or direct bonds. The cyclic or more generally "closed" ligands are rings comprising between 2 and 12 carbon atoms. Preferably, the precursor used shall have double bonds which increase the stability of such precursor. However, the precursor may possibly have no carbon double bond if desired -diene, -triene, -tetraene, or similar bounds are used instead.

Preferably, ligands such as cyclopentadienyl, cyclohexadiene, cycloheptadienyl, norbornadiene, cyclooctadienyl, cyclooctatetraene may be used. Preferably, at least, one of the carbon atoms of these closed ligands preferably all of them may independently be bounded with molecules selected from the group comprising H, alkyl groups (C<16), perfluorocarbon groups ($C_xF_{(2x+1)}$, C<16), amino compounds or any other group that may improve the characteristics of the molecules or of the resulting films.

To improve reactivity of the precursors according to the invention, it is preferred to select those precursors having one or several open-ligands (volatility will thereby increase). Allyl containing precursors are known for example to have a higher volatility than other organometallic compounds. The melting point of the various compounds exemplified hereinbelow is lower than 150° C., in order to ease the delivery up to the deposition chamber. Preferably, the melting point of a precursor according to the invention shall be at most equal to 100° C. and more preferably, at most equal to 50° C. or even below room temperature to allow its delivery as a liquid.

The high reactivity of such precursors enables low temperature deposition and less film impurities. The high volatility of the precursors according to the invention also provide high deposition rates and allows no heating of the delivery lines of the precursors. The stability of these precursors comprising molecules with an outer shell which is electronically filled is also improved. Finally the precursors according to the invention reacts with hydrogen and not oxygen (as those of the prior art), which will prevent them from generating oxygen-containing interface layer between the ruthenium film and the substrate.

DETAILED DESCRIPTION OF VARIOUS EMBODIMENTS

I—Description of Various Compounds a) Compounds including Ru(Me$_2$Cp)(Me$_2$Op)

This precursor, and more generally the ruthenium compounds of the formula Ru(R$_1$R$_2$R$_3$R$_4$R$_5$Cp)(R$_6$R$_7$R$_8$R$_9$R$_{10}$Op), wherein R$_1$ to R$_{10}$ are independently selected from the group comprising H, C1-C12 linear, branched or cyclic, Perfluorocarbon groups (Generic formula C$_X$F$_{(2X+1)}$, C<16) and, R1 to R5 comprising at least two methyl groups. The reactivity of these precursors, due to the open pentadienyl ligand, referred to as Op, is increased compared to the reactivity of Ru(EtCp)$_2$. The growth rate of the film is higher than that obtained with Ru(EtCp)$_2$ or Ru(MeCp)$_2$ counterparts, and the purity (due to the presence of a more reactive ligand) is increased.

A preferred example of this type of precursors is (1,3-dimethylcyclopentadienyl) (2,4-dimethylpentadienyl) ruthenium, (1,3-Me$_2$Cp) (2,4-Me$_2$Op) as represented hereinbelow. This precursor is a cost-effective liquid, whereas its counterpart Ru(EtCp)(2,4-Me$_c$Op), (ethylcyclopentadienyl) (2,4-dimethylpenta-dienyl) ruthenium, made of ethylcyclopentadiene is an expensive chemical. It has nevertheless a relatively high vapor pressure (around 0.1 torr at 75° C.). It is believe that the improvements are due to a better choice in the alkyl group (the presence of Me instead of Et) and to a better selection of the place of the alkyl group (for instance, Ru(1,3-Me$_2$Cp)$_2$ is reported to be a liquid while Ru(1,2-Me$_2$Cp)$_2$ is solid).

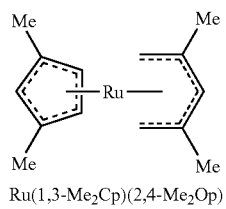

Ru(1,3-Me$_2$Cp)(2,4-Me$_2$Op)

b) Compounds including Ru(1-EtOp)2

The general formula of this family of compounds is Ru(R$_1$R$_2$R$_3$R$_4$R$_5$Op)(R$_6$R$_7$R$_8$R$_9$R$_{10}$Op), wherein R$_1$ to R$_{10}$ are independently selected from the group comprising H, C1-C12 linear, branched or cyclic, with a carbon chain on at least one of the terminal carbons (i.e., R$_1$, R$_5$, R$_6$, R$_{10}$) and perfluorocarbon groups (Generic formula C$_X$F$_{(2X+1)}$, C<16). As a specific example, Bis(1-ethylpentadienyl)ruthenium (as represented hereinbelow) is liquid because of the specific position of the alkyl groups on the pentadienyl and has a higher volatility than known related precursors. Bis(2,4-dimethylpentadienyl)ruthenium compound is solid, a drawback when delivery is considered. On a similar pattern, a better disposition of the alkyl group enhances the properties of the precursor: the melting point is decreased and the precursor is liquid.

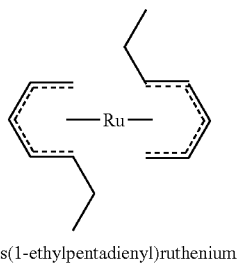

Bis(1-ethylpentadienyl)ruthenium c) Compounds including Ru(allyl)$_3$

Among the open-cycles ligands, the allyl ligand, C$_3$H$_5$, is a 3-electron donor group to the metallorganic complex. The use of allyl compounds provides higher vapor pressure than other organometallic complexes and brings higher volatility to the ruthenium tris(allyl) precursor. Furthermore, this allyl-containing complex can be used with hydrogen as a co-reactant to form ruthenium film, while oxygen is needed for other organometallics. This will allow deposition of highly pure metallic ruthenium films without oxygen impurities. Not only oxygen will be absent into the ruthenium film, but also it will not react with the substrate, preventing the creation of an undesired oxide thin layer that degrades the device's properties. The high reactivity of the open-cycle allyl group will enable the use of low temperatures depositions with high purity. Particularly, the invention relates to tris(allyl) ruthenium compounds of the formula (R$_1$CHCR$_2$CHR$_3$)(T$_1$CHCT$_2$CHT$_3$)(W$_1$CHCW$_2$CHW$_3$) Ru, wherein R$_1$, R$_2$, R$_3$, T$_1$, T$_2$, T$_3$, W$_1$, W$_2$ and W$_3$ are the same or different, independently selected from the group comprising H, C1-C12 linear, branched or cyclic, and perfluorocarbon groups (Generic formula C$_X$F$_{(2X+1)}$, C<16) More particularly, precursors of the invention comprises: tris(1-methylallyl)ruthenium, tris(2-methylallyl)ruthenium and tris(2-ethylallyl) ruthenium precursors, the latter being a liquid. Other 3-electron donor ligands can be considered, including some having a closed structure, providing compounds of the general formula RuX$_n$, where n is the number of ligands, each X being a 3-electron donor independently selected from the group comprising H, C1-C12 linear, branched or cyclic. As an example cyclopentenyl can be used.

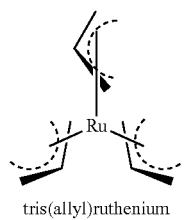

tris(allyl)ruthenium d) Compounds including RuX(allyl)$_2$

Allyl group and its useful properties can also be combined with other groups. From the base structure of the tris(allyl) ruthenium disclosed hereabove, one allyl group is substituted by a group comprising a 4 electrons donor. This 4-electron donor will enhance the stability of the molecule as an 18 electron complex is formed.

More particularly, the invention relates to Bis(allyl)RuX compounds of the formula (R$_1$CHCR$_2$CHR$_3$)(T$_1$CHCT$_2$CHT$_3$)RuX, wherein R$_1$, R$_2$, R$_3$, T$_1$, T$_2$ and T$_3$ are the same or different, independently selected from the group comprising H,C1-C12 linear, branched or cyclic. Perfluorocarbon groups (Generic formula $C_XF_{(2X+1)}$, C<16), X being selected from the group comprising cyclooctadiene, aka cod, cht, or butadiene, amidinates or any other 4 electrons donor ligands. Among such precursors, the following compounds are preferred tris(1-methylallyl)ruthenium, tris(2-methylallyl)ruthenium and tris(2-ethylallyl)ruthenium precursors. $Ru(allyl)_2(cod)$, as well as bis(2-methylallyl)(cod), are already knows as catalysts, not as ruthenium precursors for film deposition.

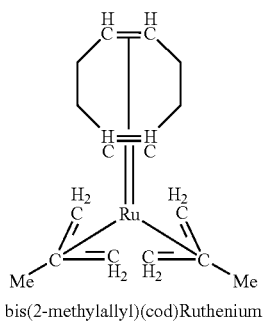

bis(2-methylallyl)(cod)Ruthenium e) $Ru(allyl)_2X_2$

The formula of this family of precursors can be written as $Ru(R_1HCHCR_2CHR_3)(R_4HCHCR_5CHR_6)X_2$, with $R_1$ to $R_6$ to be independently selected from the group comprising H, C1-C12 linear, branched or cyclic, and a perfluorocarbon group (generic formula $C_XF_{(2X+1)}$, C<16), X being be selected from the group comprising 2-electron donors, such as carbonyl, CNR, R being an low grade alkyl group (C≦4), and ethylene ($R_7R_8C$=$HCR_9R_{10}$). For example, dicarbonyl bis($\eta_3$-2-propenyl)ruthenium, is a pale yellow liquid. The electronic shell of this family is full with 18 electrons, ensuring the stability of such precursors. Vapor pressure of carbonyl containing compounds is usually high. The precursors of this family are thus stable, liquid, and highly volatile.

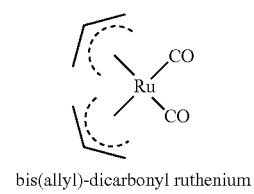

bis(allyl)-dicarbonyl ruthenium f) $Ru(CO)_x(amd)_y$

The use of amidinate ligand, whose general formula is $R_1CNC(R')NCR_2$, generates usually good quality of films from precursors containing this ligand. Each radical $R_i(R_1, R_2 \ldots R', \ldots)$ is selected from the group comprising C1-C12 linear, branched or cyclic, a perfluorocarbon group (generic formula $C_XF_{(2X+1)}$, C<16). The resulting precursors are volatile and stable. Besides, tests have shown that substantially no impurities were present in the resulting films, thereby generating high purity ruthenium films. The combination of the properties of the amidinate group with the CO group and its high volatility enables to get volatile precursors, some of them being liquid, stable, generating low impurities content films. CO can be substituted in the formula by another 2-electron donor such as ethylene ($R_5R_6C$=$CR_7R_8$).

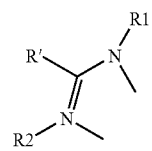

Example of an amidinate ligand

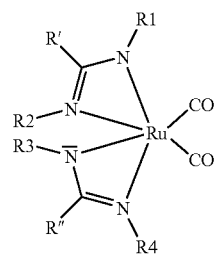

$Ru(CO)_2(amidinate)_2$ molecule

Similar ligands are known, as guadiminate and can be considered as part of the amidinate family and thus apply to the previous example. It is in fact based on the skeleton of the amidinate ligand, but the R' group is a ligand of the formula $N$—$Z_1Z_2$, where Zi is independently selected from the group comprising C1-C2 linear, branched or cyclic, and a perfluorocarbon group (generic formula $C_XF_{(2X+1)}$, C<16).

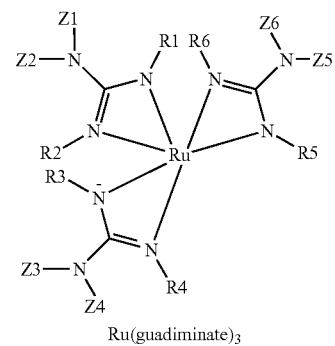

$Ru(guadiminate)_3$ g) $Ru(diketonate)_2X_2$

This family of ruthenium precursors, under the generic formula $Ru(diketonate)_2X_2$, is composed on one hand by diketonate groups, which is constituted by acac, acetylacetonate, hfac, hexafluoroacetylacetonate, tfac, tetrafluoroacetylacetonate, ofac, octafluorohexadionate, fod, heptafluorodimethyloctanedionate, TMHD, tetramethylheptdionate, and DMHD, dimethylheptadionate. The X complex is a 2-electron donor (CNR or ethylene ($R_5R_6C$=$CR_7R_8$) groups for example. No carbon neither fluorine impurities are reported in the final films. Besides, these molecules are also thermally stable below 180° C.

$Ru(diketonate)_2X_2$ family of precursors h) Ru(diketonate)$_2$(amidinate)

This family of ruthenium precursors, under the generic formula Ru(diketonate)$_2$(amidinate), is composed on one hand by the diketonate group, which comprises acac, acetylacetonate, hfac, hexafluoroacetylacetonate, tfac, tetrafluoroacetylacetonate, ofac, octafluorohexadionate, fod, heptafluoro-dimethyloctanedionate, TMHD, tetramethylheptdionate, and DMHD, dimethylheptadionate and on the other hand, by the amidinate group which can also be substituted by the guadiminate ligand. Besides, these molecules are thermally stable below 180° C.

i) O added to COD: (Ochd)RuX

Another family of precursors according to the invention is essentially consisting of the addition of an oxygen atom to a cyclohexadienyl ligand. This molecule is a 5-electron donor, similar to cyclopentadienyl or pentadienyl ligands. The chemical formula of this new ligand can be written as $R_1OCR_1CR_2CR_3CR_4CR_5CR_6$, $R_1$ to $R_6$ being independently selected from the group comprising H, C1-C12 linear, branched or cyclic and perfluorocarbon groups (Generic formula $C_xF_{(2X+1)}$, C<16). It is obvious for the man skilled in the art that any other groups or species that would increase the volatility of the compound may also be used and are included within the scope of this invention. For example (see figure below), in the $\eta^5$-oxycyclohexadienyl, the oxygen atom looses touch with the centered metallic Ru atom (it is placed at the outside of the molecule, far from the centered ruthenium atom), leading to a molecule with different properties than the cyclohexadienyl. These compounds behave more like open ligands and thus have higher reactivity and volatility, but keep the stability of the cyclic, or closed ligands.

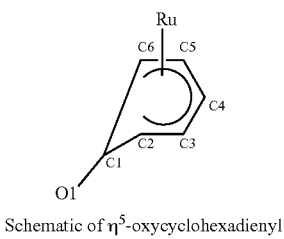

Schematic of $\eta^5$-oxycyclohexadienyl

II—Description of the Film Deposition Process

Each of the above-presented precursors has the required properties to enable ruthenium containing films deposition. Such deposition process is thereafter described. In this description the word "precursor" stands for one or a mixture of several among all of the precursors that are disclosed hereabove (with or without a solvent).

Example I

CVD Deposition

The CVD, Chemical Vapor Deposition, deposition method is characterized by mixing gases in a low pressure reactor that react together and form films on a substrate. In the present case, the ruthenium precursor is supplied from a container, in which it is stored, to the reaction chamber in which the deposition process is carried out by bubbling an inert gas into the liquid precursor or by liquid delivery injection technique. A substrate is placed in the reaction chamber (hot or cold wall) at a pre-selected temperature. The ruthenium precursor is mixed upstream or into the reaction chamber with one or several co-reactants. These co-reactants can be for example hydrogen, oxygen, a mixture of hydrogen/oxygen and/or any other gas or mixture of gases having reducing and/or oxidizing properties. The substrate's temperature is set in a range from room temperature (25° C.) to 400° C. Pressure in the reaction furnace is set in a range from 0.001 Torr to atmospheric pressure, preferably in the range 0.01-10 Torr. The ruthenium precursor and the co-reactant(s) may be transported to the reaction furnace by the use of one, several, or a mix of carrier gases. Carrier gases may for example be selected from the group consisting of nitrogen, helium, and/or argon. The deposition on the substrate is carried out during a desired period after which the feeding of all the reacting gases is stopped and the reaction chamber is purged with an inert gas. Next steps of the semi-conductor manufacturing process may then be carried out.

Example II

ALD and Related Processes (RPALD . . . ) Deposition

The ALD (Atomic Layer Deposition) deposition method is characterized by the formation of a film on a substrate whereas the gases involved are not mixed. This technique is based on a self-limiting process of adsorption on the substrate. In this example, the ruthenium precursor is supplied from a container, in which it is stored, to a reaction chamber in which the deposition process is carried out by a bubbling or liquid delivery injection technique. A substrate is placed in the reaction chamber (hot or cold wall) at a pre-selected temperature. The substrate's temperature is set in a range from room temperature (25° C.) to 400° C. Pressure in the reaction furnace is set in a range from 0.001 Torr to atmospheric pressure, preferably in the range 0.01-10 Torr. Hereinafter is a disclosed particular example of pure metallic deposition by ALD but it doesn't exclude from the scope of this invention the deposition of any other kind of ruthenium containing films by the ALD technique. The description is made with pulses of 2 co-reactants but the invention is not limited to that example and more reactants can be used. First, ruthenium precursor is allowed to enter in to the reaction chamber during a short time, thereafter called a pulse. The ruthenium precursor reacts at the surface of the substrate via an adsorption reaction until saturation of all the bonds available at the surface of the substrate. A sufficient purge by an inert gas follows in order to remove the un-reacted ruthenium precursor and the by-products present in the reaction chamber. Then a pulse of a co-reactant, which can be hydrogen, oxygen, a mixture of hydrogen/oxygen or any other gas or mixture of gases having reducing or oxidizing properties, is injected into the reaction chamber. The reactive gas reacts with the adsorbed layer deposited during the pulse of the ruthenium precursor. The groups, cyclic or open, that remained after the adsorption sequence of the ruthenium precursor, react with the co-reactant. After one cycle, the result is a pure ruthenium layer deposited on the substrate. This cycle is repeated as many times as desired on order to obtain film of the desired thickness.

In both case, the use of open ligands increased the reactivity and thus the reaction rate will be enhanced. Growth rates should therefore be higher. Their high reactivity should also enable to use only hydrogen gas as a co-reactant to reduce the precursor. The reaction of hydrogen with the adsorbed ruthenium layer might be enhanced through the use of a remote plasma, or any mean allowing the formation of hydrogen radicals or excited hydrogen gas. Oxygen may then not be necessary from the process, which will avoid the oxidation of the underlying layer, which brings out damages to the device.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for depositing a ruthenium containing film into a reactor onto a substrate comprising the steps of:
   a) providing a substrate into the reactor, at reaction temperature;
   b) introducing at least one ruthenium containing precursor into the reactor, wherein the precursor comprises at least one precursor selected from the group consisting of: Ru(diketonate)$_2$X$_2$; Ru(diketonate)$_2$ (amidinate)$_2$; their derivatives, and mixtures thereof; wherein:
      the diketonate group comprises at least one member selected from the group consisting of: acetylacetonate; hexafluoroacetylacetonate; tetrafluoroacetylacetonate; octafluorohexadionate; heptafluoro-dimethyloctanedionate; tetramethylheptdionate; and dimethylheptadionate;

X comprises a 2-electron donor complex; and the amidinate comprises an amidinate group with the general formula:

$R_1CNC(R')NCR_2$ wherein each radical $R_i(R_1, R_2, R')$ is independently selected from the group consisting of: C1-C12 linear, branched, or cyclic alkyl groups; and a perfluorocarbon group of the general formula $C_xF_{(2x+1)}$, where x is less than 16;

c) introducing into the reactor a gas mixture comprising hydrogen and/or oxygen; and
   d) reacting the ruthenium containing precursor and the gas mixture to deposit a ruthenium containing film onto the substrate.

* * * * *